United States Patent
Jansson et al.

(10) Patent No.: US 9,167,832 B2
(45) Date of Patent: Oct. 27, 2015

(54) LOW FLOURIDE CRUSTACEAN CONCENTRATED HYDROLYSATE FRACTION COMPOSITIONS

(71) Applicant: Emerald Fisheries AS-Olympic Seafood, Alesund (NO)

(72) Inventors: Stig Tore Kragh Jansson, Tromvn (NO); Jon Reidar Ervik, Lerstadtoppen (NO); Leif Grimsmo, Haugstien (NO)

(73) Assignee: EMERALD FISHERIES AS, Alesund (NO)

( * ) Notice: Subject to any disclaimer, the term of this patent is extended or adjusted under 35 U.S.C. 154(b) by 0 days.

(21) Appl. No.: 14/074,392

(22) Filed: Nov. 7, 2013

(65) Prior Publication Data

US 2014/0178489 A1   Jun. 26, 2014

Related U.S. Application Data

(62) Division of application No. 13/063,488, filed as application No. PCT/NO2009/000322 on Sep. 14, 2009, now Pat. No. 8,758,829.

(30) Foreign Application Priority Data

Sep. 14, 2008  (NO) .................................... 20083906

(51) Int. Cl.
| A61K 35/64 | (2015.01) |
| A23J 1/04 | (2006.01) |
| A23L 1/015 | (2006.01) |
| A23L 1/305 | (2006.01) |
| A23L 1/33 | (2006.01) |
| A61K 35/612 | (2015.01) |

(52) U.S. Cl.
CPC .................. *A23J 1/04* (2013.01); *A23L 1/0153* (2013.01); *A23L 1/3053* (2013.01); *A23L 1/33* (2013.01); *A61K 35/612* (2013.01)

(58) Field of Classification Search
None
See application file for complete search history.

(56) References Cited

U.S. PATENT DOCUMENTS

| 5,053,234 | A | 10/1991 | Anderson et al. | 426/59 |
| 5,210,186 | A | 5/1993 | Mikalsen et al. | 530/418 |
| 6,555,155 | B2 | 4/2003 | Saxby et al. | 426/56 |
| 6,800,299 | B1 | 10/2004 | Beaudoin et al. | 424/522 |
| 2008/0274203 | A1 | 11/2008 | Bruheim et al. | 424/522 |
| 2011/0217386 | A1 | 9/2011 | Jansson et al. | 424/538 |
| 2011/0224450 | A1 | 9/2011 | Sclabos Katevas et al. | 554/23 |

FOREIGN PATENT DOCUMENTS

| EP | 0785029 B1 | 7/1997 |
| EP | 1 417 211 B1 | 5/2007 |
| FR | 2835703 | 8/2003 |
| GB | 2240786 | 8/1991 |
| JP | S5264453 A | 5/1977 |
| JP | S55141166 | 4/1980 |
| JP | H2215351 | 8/1990 |
| JP | 03139291 | 6/1991 |
| JP | H05507624 A | 11/1993 |
| JP | H07194314 A | 1/1995 |
| JP | 2843669 B2 | 1/1999 |
| JP | H11123052 A | 11/1999 |
| JP | 2001511008 | 8/2001 |
| JP | 2003199510 A | 7/2003 |
| JP | 2008500040 A | 1/2008 |
| NO | 324487 | 10/2007 |
| NO | 325805 | 7/2008 |
| NO | 20083906 | 9/2008 |
| WO | WO00/23546 | 4/2000 |
| WO | WO02/102394 | 12/2002 |
| WO | WO02102394 A2 | 12/2002 |
| WO | WO2008/060163 A1 | 5/2008 |
| WO | WO2008072563 A1 | 6/2008 |
| WO | WO2010/030193 | 3/2010 |

OTHER PUBLICATIONS

Tenuta et al., Acta Alimentaria, 1993, vol. 22, No. 4, p. 269-281.*
Sidhu et al., J. Sci. fd. Agric, 1970, vol. 21, p. 293-296, "Biochemical composition and Nutritive value of Krill".*
Kawamura et al., JARQ, 1992, vol. 26, p. 210-213.*
Alvarez, et al., "Lipds in pharmaceutical and cosmetic preparations." Grasas y Aceites 51(1-2):74-96 (2000).
Murphy, et al., "Fatty Acid and Sterol Composition of Frozen and Freeze-Dried New Zealand Green Lipped Mussel (Perna Canaliculus) from Three Sites in New Zealand." *Asia Pac J Clin Nutr.*,12(1):50-60 (2003).
Tenuta, "Fluorine removal during production of krill paste and krill protein concentrates." *Acta Alimentaria—Academiae Scientiarum Hungaricae*; 22:4:269 abstract only (1993).
Tou, et al., "Krill for Human Consumption: Nutritional Value and Potential Health Benefits." *Nutr Rev.*, 65(2):63-77 (2007).
Yoshitomi et al., "Effect of total replacement of dietary fish meal by low fluoride krill (*Euphausia superba*) meal on growth performance of rainbow trout (*Oncorhynchus mykiss*) in fresh water," *Aquaculture*, 266:219-225 (2007).
Zanardi, et al., "Lipid and Colour Stability of Milano-Type Sausages: Effect of Packing Conditions." *Meat Sci.*, 61(1):7-14 (2002).
NPL Search results (Google Scholar) Jun. 13, 2013.
NPL Search results (Google Scholar) Nov. 13, 2013.

(Continued)

*Primary Examiner* — Kade Ariani
(74) *Attorney, Agent, or Firm* — Medlen & Carroll, LLP

(57) ABSTRACT

Fluorine being present in the exoskeleton of crustaceans, and especially krill represents a problem for using krill as a source for food, feed, food additives and/or feed additives. There has been developed a process for removing such fluorine from krill material by subjecting the krill to disintegration and to an enzymatic hydrolysis process prior to or simultaneously with a removal of the exoskeleton particles producing a fluorine-reduced product. Inherent in the disclosed process is the ability to process krill material with a high polar lipid content for producing superior quality, low fluorine, products suitable for the food and feed as well as the pharmaceutical, nutraceutical and cosmetic industry.

9 Claims, 1 Drawing Sheet

(56) References Cited

OTHER PUBLICATIONS

Kolakowski, et al. "Improvement in partial-autoproteolysis process for obtaining chitin-free low fluoride content protein precipitate from Antarctic krill", Proceedings of the 6th International Congress of Food Science and Technology, Dublin, Sep. 18-23, 1:168 (abstract only) (1983).

Norwegian Office Action corresponding to Norwegian application No. 20083906 dated Mar. 30, 2009.

Notification of Transmittal of the International Search Report and the Written Opinion of the International Searching Authority, or the Declaration corresponding to International Application No. PCT/NO2009/000322 mailed Dec. 16, 2009.

Miniadis-Meimaroglu et al., "Isolation and identification of phospholipids molecular species in a wild marine shrimp *Penaeus kerathurus* muscle and cephalothorax," *Chemistry and Physics of Lipids*, 152:104-112 (2008).

Slizyte et al., "Enzymatic hydrolysis of cod (*Gadus morhua*) by-products optimization of yield and properties of lipid and protein fractions," *Process Biochemistry*, 40:3680-3692 (2005).

Macias-Sanchez et al., "Extraction of carotenoids and chlorophyll from microalgae with supercritical carbon dioxide and ethanol as cosolvent," *J. Sep. Sci.*, 31:1352-1362, Abstract (2008).

Turgut et al., "Extraction of Phospholipids from Canola with Supercritical Carbon Dioxide and Ethanol," *JAOCS*, 72(9):1009-1015 (1995).

Yamaguchi, "Supercritical Carbon Dioxide Extraction of Oils form Antartic Krill," *J. Agric. Food Chem*, 34(5): 904-907 (1986).

Soxhlet F., "Die gewichtsanalytische bestimmung des milchfettes" *Dingler's Polytech.* J. 232:461-465 (1879).

Neptune Krill Oil Supplement facts,—NOW Supplements, from nowfoods website, 2 pages, downloaded on Aug. 18, 2014.

Vazhiyil Venugopal, "Marine Products for Healthcare: Functional and bioactive Nutraceutical Compounds from the Ocean." CRC Press,—Technology & Engineering, Only p. 248, Oct. 20, 2008.

Saether, et al., "Lipids of North Atlantic Krill." Journal of Lipid Research, 27:274-285 (1986).

Manthey, et al.: "Reduction of the fluoride content of krill by acid treatment. (translated)", Informationen Fuer Die Fischwirtschaft, Hamburg, De, vol. 30, No. 2: 102-106 (1983).

Yancey, 'Organic osmolytes as compatible, metabolic, and counter-acting cytoprotectants in high osmolarity and other stresses' J. Exp. Biol. 208(15): 2819-2830 (2005).

Anonymous: "Krill Oil", XP002698327, Database accession No. 1651779.Database GNPD [Online] MINTEL; (Apr. 1, 2010).

Anonymous: "Krill Oil Food Supplement", XP002698326, Database accession No. 1316439 Database GNPD [Online] MINTEL; (Oct. 1, 2011).

Gigliotti, et al., "Extraction and characterisation of lipids from Antarctic krill (*Euphausia superba*)", Food Chemistry, Elsevier Ltd, NL, 125(3):1028-1036 (Apr. 1, 2011), XP027477867, ISSN: 0308-8146, DOI: 10.1016/J.FOODCHEM.2010.10.013 [retrieved on Nov. 4, 2010].

Jung, et al., "Decreasing effect of fluoride content in Antarctic krill (*Euphausia superba*) by chemical treatments", International Journal of Food Science and Technology, 48(6): 1252-1259, XP055064993, (Feb. 4, 2013).

Martin, "Antarctic krill" (Le Krill Antarctique), Phytothérapie; De La Recherche À La Pratique, Springer-Verlag, PA, 5(1): 6-13, XP019521841, (Aug. 1, 2007).

"Neptune Krill Oil's Unique Properties", XP002660404, Internet Citation, Sep. 30, 2011, pp. 1-3, Retrieved from the Internet: www.nowfoods.com/Products/ProductFAQs/081008/htm [retrieved on Sep. 30, 2011].

Sands, et al., "Fluoride in Antarctic marine crustaceans", Marine Biology, 132(4):591-598, XP055064990, (Dec. 9, 1998).

Tenuta, Filho, "Fluorine removal during production of krill paste and krill protein concentrates." Acta Alimentaria—Academiae Scientiarum Hungaricae; 22:4:269 (1993).

\* cited by examiner

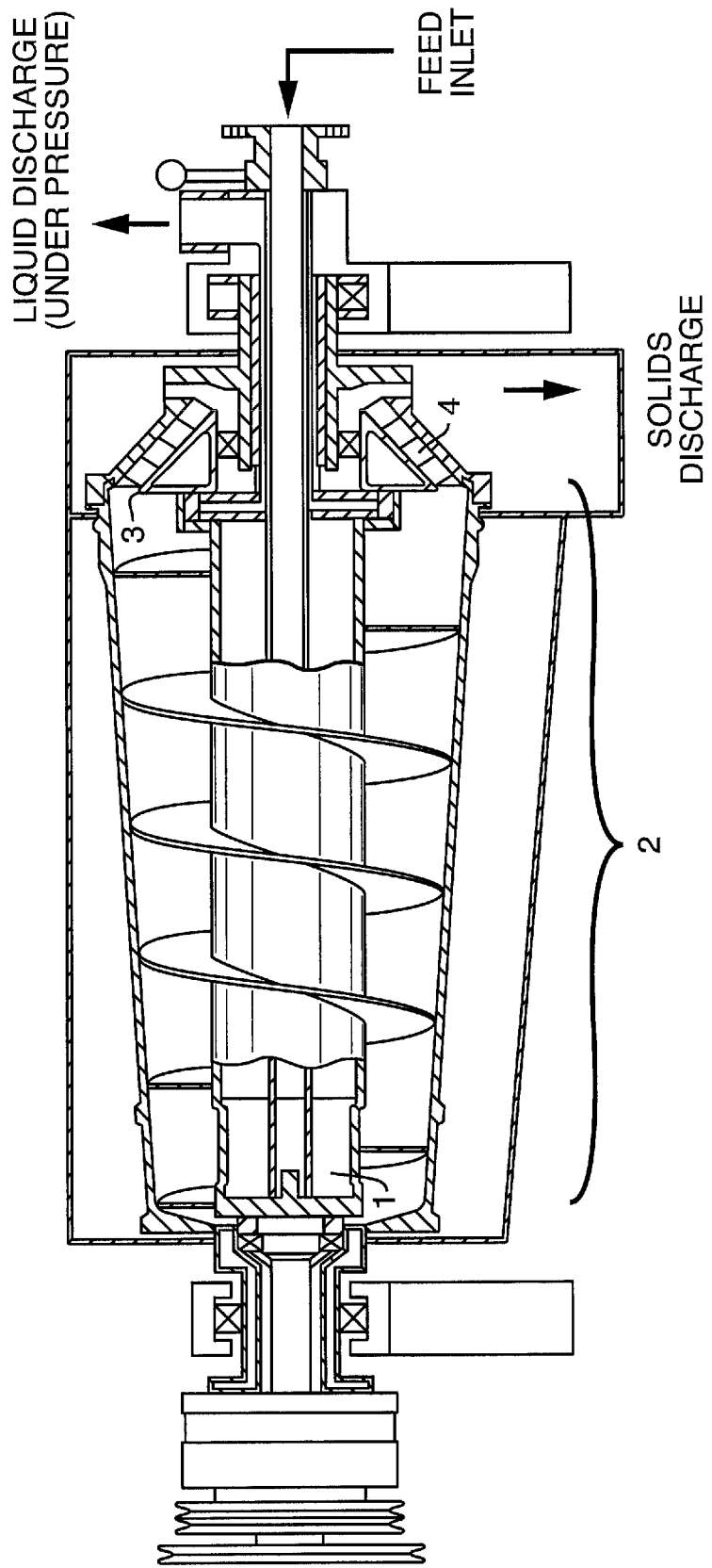

LOW FLOURIDE CRUSTACEAN CONCENTRATED HYDROLYSATE FRACTION COMPOSITIONS

The present invention concerns an industrial method for removing fluoride and unwanted trace elements contained in crustaceans. The process is especially favourable and effective for substantial reduction of fluoride from krill by removing substantial amounts of the shell and carapace and forming several fractions from the crustaceans, inter alfa a fluoride-reduced lipidaceous and proteinaceous emulsion. The invention also solves processing problems related to such emulsions caused by high lipid content, and especially high polar lipid content with lipids such as phospholipids. The produced end products obtained by the process according to the invention may be used per se as food or feed, as food/feed additives, as nutraceuticals, cosmaceuticals/cosmeticals or pharmaceuticals or used as starting materials for further downstream processing. The process according to the invention is also suitable to be used on other crustaceans than krill.

BACKGROUND FOR THE INVENTION

A problem not sufficiently addressed by the prior art is the fluoride and unwanted trace material content included in the shell, carapace and crust of crustaceans. In the disclosure infra the notion "krill" is used, signifying that krill is one kind of crustaceans wherein this problem is especially accentuated, but also other types of crustaceans are relevant in the present invention. Another problem related to krill, and especially the Antarctic krill, is the high content of polar lipids during the second half of the fishing season.

As mentioned a well known problem when processing Antarctic krill (*Euphausia superba*) is that the lipid content, and especially the polar lipid content such as phospholipids, can be very high during the second half of the season from April/May to June/July.

As a rule for most known animal species the content of polar lipids, such as phospholipids, is nearly constant and variations in total lipid content is caused by variations in the content of neutral lipids such as triglycerides. Despite these very high variations of lipid content, the ratio between triglycerides and phospholipids is nearly constant for the Antarctic hill. It is also well known that lipids, and especially phospholipids, cause strong emulsions. Such emulsions cause problems in the separation of the fractions in the processes, such as hydrolysis, which involves separation of lipid- and proteinaceous fractions. The developed process according to the present invention also solves the emulsion problems by creating an aggregate of non-soluble proteins and phospholipids before and during the last separation step in the process.

Krill represent a vast resource for biological material. The amount of Antarctic krill (*Euphausia superba*) which live in the Antarctic Ocean, although varying depend on the calculation method and investigation, is roughly 1 to $2 \times 10^9$ tons and the possible weight of catch is estimated at 5 to $7 \times 10^6$ tons. These small crustaceans that live in the cold waters around the Antarctic, are interesting as a source for proteins, lipids such as phospholipids, poly-unsaturated fatty acids etc., chitin/chitosan, astaxanthin and other carotenoids, enzymes and other materials, and several methods for isolating such materials have been developed.

The background for the present invention resides in the circumstance that krill accumulate fluoride in their shell, increasing the fluoride amount of any produced material either through the inclusion of such shell parts, through extraction processes not taking into account the transfer of fluoride to the final material through the extraction steps or through time-consuming processes wherein free fluoride or loosely bound fluoride may diffuse from the shell material and into the further processed material, making the end product high in fluoride ions or fluorinated compounds.

Fluoride is a compound that in high concentrations is detrimental for the health of land-dwelling animals as well as all kind of fish and crustaceans and especially fresh-water fish species, since fluoride atoms have the tendency of entering into the bone structure of such organisms and creating fluorosis (a weakening of the bone structure similar in its effect to osteoporosis, but different since it is the bone structure itself, and not the porosity of the bone that is affected). Skeletal fluorosis is a condition characterised by skeletal abnormalities and joint pain. It is caused by pathological bone formation due to the mitogenic action of fluoride on osteoblasts. In its more severe forms, skeletal fluorosis causes kyphosis, crippling and invalidism. Secondary neurological complications in the form of myelopathy, with or without radiculopathy, may also occur. High fluoride intake has also been shown to be toxic to the male reproductive system in rat experiments, and in humans high fluoride intake and symptoms of skeletal fluorosis have been associated with decreased serum testosterone levels.

Consequently, if krill material is to be used as a starting material for food or feed products, precautions have to be taken for removing fluoride through the processing steps. However, the diffusion of fluoride and the presence of miniscule krill shell material represent a problem that is most difficult to overcome when processing krill material in an industrial scale.

Additionally it can be advantageous to reduce the ash content including trace elements from the proteinaceous material produced from the catch.

Thus there exists a need for an industrial method producing proteinaceous materials and lipids from krill wherein fluoride is cost-effectively removed for producing products with significantly reduced fluoride content.

Polar lipids such as phospholipids are essential for cell membranes and are also called membrane lipids. Normally the total lipid content in fish and other aquatic and terrestrial animals varies due to variations in feed accessibility through the year. The variations is normally caused by variations in the content of non polar lipids in the organisms which is stored and used as energy reserves during periods of low or no access to feed, while the content of phospholipids is relatively constant. However, for Antarctic krill this is different because the relative content of triglycerides and phospholipids remains almost constant also when the fat content in this species varies from 2% up to 10% during the fishing/harvesting season. This means that the phospholipid content in raw Antarctic krill can be up to 5%. Lipids, and especially polar lipids as phospholipids, are known to create strong emulsions in industrial processing according to prior art which involves heating-, stirring- and separation steps such as a hydrolysis process. This emulsion will normally cause problems in separating the lipid- and protein fractions.

Thus there also exists a need for an industrial method for elimination of separation problems caused by emulsion when producing proteinaceous concentrates from krill.

There also is a need for a versatile industrial method addressing both the removal of fluorine from the processed krill material and the varying contents of polar lipids in the krill material.

PRIOR ART

In FR patent 2835703 (Applicant: Techniagro, Inventor: Fanni, J. et al., Mar. 15, 2002) there is disclosed an isolation method for obtaining a protein hydrolysate from a marine source such as filleting discards and other marine waste materials (among others shellfish). The patent includes steps of crushing, hydrolysis, filtration and centrifugation, but is not particularly suited for processing krill and certainly does not concern itself with the problem of removing fluoride from the material.

Also the sequence of steps in any processing method has an impact on the quality and composition of the final product. Thus the above mentioned process according to Fanni does not produce, nor is suitable, for removing fluoride from the processed material.

Also the process according to Fanni does not address the problem with high polar lipid content in the processed material, and offers no solution to this problem.

In EP patent 1 417 211 B1 (Neptune Technologies & Bioresources, Inc.) there is disclosed a composition including a particular phospholipid and a particular flavonoid and the use thereof for producing a medicament suitable for treating or preventing a number of diseases. The composition is produced from natural marine or aquatic sources, inter alia krill (*Euphausia superba*, Antarctic krill and *Euphausia pacifica*, Atlantic krill) as well as krill from the Indian Ocean, Mauritius Islands and or Reunion Island off Madagascar, the Canadian West coast, the Japanese Coast, the Gulf of St. Lawrence and the Bay of Fundy and other krill habitats. The method for extracting the relevant phospholipid and flavonoid is described to be by a method carried out by successive acetone and alcohol treatments after an initial milling/crushing step. Again there are no precautions taken for removing the fluoride from the material, and actually the produced product, albeit containing the indicated phospholipid and falvonoid, has in no way the same composition as the product according to the present invention at least for the reason that the present process includes no acetone or alcohol extractions, and also includes a number of mechanical steps for removing solid krill material from the initial krill mass.

In GB patent 2 240 786 (Korea Food Research Institute) the problem with the high fluoride content of hill is recognized, but there is proposed passing electric current through pulverized krill for removing fluoride using aluminium electrodes, not taking into account the problem with actually removing the fine particles from the crushed krill substance, thus potentially removing the free fluoride but instead creating other problems concerning the removal of the fine particles and also not taking into account the rather large amounts of bound fluoride that still is present in the miniscule shell particles remaining in the electrolysed material.

In U.S. Pat. No. 5,053,234 (Anderson et al.) there is disclosed a proteinaceous product produced through a process involving a milling stage, a hydrolyzing stage using proteolytic enzymes, an inactivating stage involving heating of the material and simultaneously producing an oil through the heating, a screening stage for removing water from the product, and a subsequent oil-separation stage for removing oil to form the final product. Again nothing is indicated concerning removing fluoride from the material.

GENERAL DISCLOSURE OF THE INVENTION

The present invention provides an industrial method for processing catches of hill comprising a number of steps presenting a very early and substantially complete removal of crust, carapace and shell and thereby a substantial removal of fluoride from the krill material. The method also prevents separation problems caused by emulsions when processing a raw material with high content of phospholipids.

The method according to the present invention is initiated immediately subsequent to decking a catch of krill. It is of importance that the method according to the present invention is initiated as soon as possible after the catch of krill has been decked since fluoride immediately starts to leak/diffuse from the crust and carapace into the flesh and juices from dead krill.

When using the term "immediately" in connection with starting the process according to the present invention this relates to the period from decking the krill catch and to the initial disintegration of the hill (see infra). This period of time should be kept to a minimum, and should preferably not exceed 60 minutes, more preferred not exceed 30 minutes, even more preferred not exceed 15 minutes, and should include a direct transfer of the krill catch from the trawl bag/net to a suitable disintegrator. A disintegrator of the krill material may be a conventional pulping, milling, grinding or shredding machine.

The krill catch is initially loaded into an apparatus for disintegration of the raw material through e.g. pulping/milling/grinding/shredding. The temperature of the disintegration process is around the ambient temperature of the water, i.e. between $-2$ and $+10°$ C., preferably around $+0°$ C. to $+6°$ C., and may be performed by any convenient disintegration method. This disintegration process is also conventionally done by the previous known processing methods, and represents one of the obstacles according to the prior art because it produces large amounts of shell and crust debris from the krill mixing in the milled material and producing a disintegrated paste with a high fluoride content. However, this high fluoride content is one of the reasons why the prior art processed hill material has limited applications and is less suitable for food, feed or corresponding food or feed additives compared to other marine raw materials e.g. pelagic fish.

According to the present invention the krill material is divided into a particle size suitable for a further separation step for not interfering with the subsequent processing steps.

The disintegrating process is performed continuously and causes a particles sizes up to 25 mm, preferred particle size is 0.5-10 mm and more preferred 1.0-8 mm. The particle size distribution represents one of the aspects of the invention because the fluoride has a tendency to leak out of the milled material and mingle with the rest of the raw material. However, this leaking process takes time and is not as rapid as being preventive for a subsequent enzymatic hydrolysis step, provided the hydrolysis step is performed within specific parameters with respect to time and optimal or near-optimal conditions such as pH and temperature and optionally with the addition of co-factors such as specific ions depending on the used enzymes.

The temperature of the disintegrated material shall according to the present invention be elevated to a temperature suitable for the subsequent enzymatic hydrolysis. The temperature shall be increased as soon as possible (within seconds [e.g. 1-300 seconds, more preferred 1-100 seconds, even mo preferred 1-60 seconds, most preferred 1-10 seconds]) subsequent to the disintegrating step for reducing the processing time and thereby preventing diffusion of fluoride and for preparing the material for the enzymatic hydrolysis.

According to the present invention enzymes may be added directly to the disintegrated material or through the added water or both, before, during or after the disintegration process.

According to the present invention exogenous proteolytic enzymes (e.g. alkalase, neutrase, and enzymes derived from microorganisms [*Bacillus subtilis, Aspergillus niger*, etc] or plant species) shall be added before, during or after the disintegration, and before, during or after the heating of the disintegrated material. The added enzyme(s) may be in the form of one single enzyme or a mixture of enzymes. The conditions of the hydrolysis should match the optimal hydrolytic conditions of the added enzyme(s) and the selection of optimal conditions for the selected exogenous hydrolytic enzyme(s) is known to the person skilled in the art. As an example the exogenous enzyme alkalase having a pH optimum of about 8, a temperature optimum of 60° C. and a hydrolysis time of 40-120 minutes. The selected enzymes, or combination of enzymes, should also be chosen for reducing emulsions caused by high content of phospholipids in the raw material.

The efficient amount of proteolytic enzyme(s) will be set after a process- and product optimization, and will also depend on the efficiency of the specific chosen commercial enzyme or mix of enzymes. A typical amount by weight of commercial enzymes, as a ratio of the amount of the weight of the disintegrated raw material, are preferably between 0.5% and 0.05%, more preferably between 0.3% and 0.07% and most preferable between 0.2% and 0.09%. Fresh caught hill is known for rapid and uncontrolled autolysis by endogenous (natural) enzymes.

The reason for adding exogenous enzymes is to take control of, and guide, the breakdown of the proteinaceous material in the disintegrated substance as well as aiding in speeding up/accelerating the hydrolysis of the material (see infra) on account of avoiding/preceding the leaking of fluorine from the shell, carapace and crust as mentioned supra. The enzymes, or the combination of enzymes, should also be carefully chosen to reduce emulsion in the production process. Enzymes may be selected from exo- and/or endopeptidases. If a mixture of enzymes is used, such a mixture may also include one or more her chitinases for subsequently making the chitin-containing fraction(s) more amenable to further downstream processing. If chitinases are used care must be taken for not increasing the leakage of fluorine from the shell/crust/carapace of the krill into the other fractions. However, since such fluorine leakage takes time, it is possible to perform such an enzymatic treatment within the time parameters indicated supra. A more convenient alternative to including chitinases in the enzyme mix of the initial hydrolysis step will be to process the separated chitin-containing fraction subsequently to the separation step.

As it is important to avoid the leaking of fluoride from the milled material, and since the leaking to some degree is related to the increased surface area created through the disintegrating step, the enzymatic hydrolysis step should be finished within a time interval of 100 minutes, preferably within 60 minutes, most preferred within 45 minutes calculated from the addition of the endogenous enzyme(s). The amount of enzyme(s) added is related to the type of enzyme product used. As an example it may be mentioned that the enzyme alkalase may be added in an amount of 0.1-0.5% (w/w) of the raw material. This should be taken into context with the added endogenous enzymes since the addition of more enzymes will reduce the time interval of the hydrolytic step. As mentioned supra the time of the hydrolytic step is one of the crucial features of the present process since a short hydrolysis time reduces the diffusion time of fluorine from shell, carapace and crust particles. The hydrolytic enzymatic processing step is intended to remove the binding between the soft tissue of the krill to the external shell, crust and carapace of the crustacean.

Subsequent to or together with the hydrolytic processing step the krill material is passed through a particle removal device operating through a gravitational force such as a decanter. This separation step removes the fine particles containing a considerable amount of the fluoride from the hydrolysed or hydrolysing krill material. The decanter is operated with a g force between 1.000 and 1.800 g, more preferably between 1.200 and 1.600 g and most preferably between 1.300 and 1.500 g. Through this particle removal step a substantial amount of fluorine is removed from the proteinaceous krill fraction. The reduction of fluorine on a dry weight basis as compared to conventional krill meal, with a typical fluorine content of 1.500 p.p.m, may be up to 80%, even more preferred up to 85%, most preferred up to 95%.

The enzymatic hydrolysis may be terminated by heating of the hydrolysing material (incubate) to a temperature over 90° C., preferably between 92-98° C. and most preferred between 92-95° C., prior to, during or after the separation step, as long as the hydrolysis duration lies within the above given boundaries. The hydrolysis is terminated before, during or after the fine particle removal step, most preferred after the fine particle removal step. The temperature of the decanter particle removal step will in one embodiment depend on the optimal activity temperature of the enzyme (in the case where the enzymatic hydrolysis step is terminated by heating after the fine particle separation step).

The fluorine content in the prior art processed krill protein material has limited applications and are less suitable for food or feed or corresponding food or feed additives, as mentioned supra but the fluorine content of the removed shell material is not preventive for further separation/purification of this fraction. Thus materials such as chitin, chitosan and astaxanthin may be isolated from the separated shell material. Such isolation procedures are known within the art. Steps may also be taken for removing the fluorine from the isolated shell material e.g. through dialysis, nanofiltration, through electrophoresis or other appropriate technologies.

The hydrolytic enzyme(s) is/are deactivated. Such deactivation may be performed in different ways, such as adding inhibitors, removing co-factors (e.g. crucial ions through dialysis), through thermal inactivation or any other deactivating means. Among this thermal inactivation, as mentioned supra, is preferred by heating the proteinaceous material to a temperature where the hydrolytic enzymes become denatured and deactivated. However, if a product where the relevant native proteins are not denatured is wanted, other means than heating for deactivating the hydrolytic enzymes should be selected.

The proteinaceous material exiting the decanter forms a de-fluorinated incubate and may be separated forming a Phospholipids/Peptide Complex (PPC), a lean hydrolysate fraction as food or feed additives and a lipid fraction mainly consisting of neutral lipids.

The PPC is rich in lipids, like a smooth cream with no particles, and is well suspended in the proteinaceous material. This gives small density differences in the material and makes it difficult to separate with common centrifugal separators and decanters. This is especially accentuated with krill catches during the second half of the fishing season.

Ordinary disc centrifugal separators would not work properly since emptying and necessary cleaning cycles with water will disturb separation zones, cause emulsions in products with high phospholipids content, and result in low dry matter concentrations of PPC. Standard decanters would not have possibility to separate due to low g force, short separation zone and intermixing of light and heavy phase at the discharge of heavy phase from the machine. The separation of the proteinaceous material into sub-fractions will therefore preferably be performed by a specially designed horizontal decanter centrifuge with an extended separation path as shown in FIG. 1 below.

The specially designed decanter is essentially a decanter centrifuge but with some novel differences. As for ordinary decanters, the feed enters the bowl through a central placed feed pipe in the middle of the separation zone. In this special decanter the feed enters at the end and at the opposite side of the outlet (1.). This gives the feature of a considerably longer clarification/separation zone than ordinary decanters and utilizes the total available separation length (2.) of the machine. The drive is able to impart high g-forces: 10 000 g for small machines and 5 000 to 6 000 g for high capacity machines, facilitating the separation of very fine, slow-settling PPC without emulsification. The concentrated PPC will be subjected to the highest g-force just before entering under the baffle (3.). The different liquid layers from PPC are concentrated gradually and the PPC can solely escape under the baffle, be pressurised by the g force and pushed out by the machine (4). The concentration of the PPC to about 27-30% dry matter makes the downstream processing efficient in terms of operating/robustness and as well economically considering both yield and costs for drying of PPC to a meal. It is also of importance to have a good separation in this step to get a lean hydrolysate without disturbing macromolecules being able to concentrate the hydrolysate by evaporation to a final concentration of more than 60%.

The lipid content in the PPC on dry matter basis is reflected by the seasonal variations of the lipid content in the raw material and is typically around 50%. The fluorine reduction on dry weight basis compared to commercial krill meal in the PPC is preferably over 70%, more preferred over 75% and most preferred over 80%.

The dry matter content in the CHF (Concentrated Hydrolysate Fraction) after separation and after evaporation is preferably over 45%, more preferred over 50% and most preferred over 55%. The lipid content in the CHF on dry matter basis is preferably below 5%, more preferred below 4% and most preferred below 3%. The fluorine reduction on dry weight basis compared to commercial krill meal in the CHF is preferably over 85%, more preferred over 90%, most preferred over 96%.

While the CHF has a low lipid content and a low water activity ($a_w$<0.79) this fraction could be stored in a temperature below 4° C. for more than 12 months without any significant microbial growth or other degradation of the product.

The lipid oxidation in marine lipids proceeds relatively rapidly also during cold storage, being the reason why the process according to the invention should be conducted on fresh caught material onboard a fishing vessel. The PPC may be frozen, but the best industrial and cost efficient way to provide a storage-stable product is, however, to dry the PPC, preferably in a gentle drying process with low temperatures (0-15° C., e.g. 1-10° C. or 2-8° C.) and under inert conditions. This gives a reduced oxidative stress on the long-chain polyunsaturated omega-3 fatty acids (n-3 LCPUFA). A lyophilisation process is also well suited since this avoids an overheating of the product.

Furthermore, an improved product may be obtained by vacuum (pressure . . . ? mm Hg) and low temperature (within the interval supra) and scraped surface drying of the PPC.

The unique low-fluoride-containing dried PPC product is well suited for pharma production, human consumption such as nutraceutical products, food ingredient products, human consumption in general and special ingredients in feed.

The dried PPC is well suited for further downstream processing of the separate substances of interest, especially since water has been removed. This makes a succeeding extraction process significantly simpler and more cost efficient compared to extraction of raw/thawed material.

The storage stability of the PPC meal is extraordinarily good on account of low initial values of oxidation products being present in the fresh catch. The PPC meal is preferably produced in an inert atmosphere, packed under an inert atmosphere and in a packaging with a good oxygen barrier, prolonging the storage life period significantly.

EXAMPLE

A fraction of 500 kg from a 10 ton catch of Antarctic krill was immediately (maximally 20 minutes after catch) shredded through a knife cutter into pieces of a particle size of 3-6 mm at a temperature of 1-2° C., and immediately thereafter added 500 liters fresh water and alkalase in an amount of 0.2% (w/w) of the hill wet weight and then heated to a temperature of 55-60° C.

The enzyme was allowed to function for 45 minutes at said temperature. The material was thereafter fed to a decanter operated at the following conditions: Temperature: 90° C., gravity force at 1400 g and with a feed rate of 1.2 ton krill/water/enzyme suspension per hour causing a separation of the fluorine-containing fine particles and a liquid proteinaceous fraction exiting the decanter. The material was then heated to a temperature of 93° C. in order to terminate the enzymatic hydrolysis and denaturing/agglomerating the insoluble protein together with polar lipids for following separation. The liquid proteinaceous fraction was immediately thereafter transferred to a separation step by a specially designed decanter (sedicanter) mentioned supra, separating the solid phase containing insoluble proteins and polar lipids concentrate (PPC) from the hydrolysate.

The PPC are thereafter mixed with a food-grade anti-caking agent, dried in a thin film vacuum drier and packed in air tight bags under nitrogen atmosphere. The aqueous soluble protein (hydrolysate) and neutral lipid phase are feed to a separator separating the neutral lipid phase from the hydrolysate. The oil is stored in air tight containers under nitrogen atmosphere.

The hydrolysate are continuously feed into a flash evaporator for dewatering/concentration giving a concentrated hydrolysate fraction (CHF) with dry weight of 55-70% and stored in air tight containers under nitrogen atmosphere.

A typical mass balance for processing of raw lean Antarctic krill is shown in table below:

TABLE I

Mass balance for processing of raw lean Antarctic krill.

| Fraction | From 500 kg raw krill | Dry weight in fraction |
|---|---|---|
| PPC (Phospholipids/Peptide Complex) | 80 kg | 28% |
| Dried PPC (with anti-caking agent) | 25 kg | 97% |
| Hydrolysate | 770 kg | 6.1% |
| CHF (Concentrated Hydrolysate Fraction) | 78 kg | 60% |
| Fluorine-containing fine particles (shell and carapace fragments) | 45 kg | 40% |
| Neutrals oils | <5 kg | 100% |

BRIEF DESCRIPTION OF THE DRAWING

FIG. 1. A specially designed decanter with an extended separation path. This example is a FLOTTWEG SEDICANTER® horizontal decanter centrifuge.

The invention claimed is:

1. A concentrated krill protein hydrolysate fraction prepared by enzymatic hydrolysis of krill comprising a fluoride reduction of at least 85% on dry matter basis as compared to an approximate 1,500 ppm fluoride value in commercial krill meal.

2. The concentrated hydrolysate composition of claim 1, having a fluoride reduction of at least 90% on dry matter basis as compared to an approximate 1,500 ppm fluoride value in commercial krill meal.

3. The concentrated hydrolysate composition of claim 1, having a fluoride reduction of at least 96% on dry matter basis as compared to an approximate 1,500 ppm fluoride value in commercial krill meal.

4. The concentrated hydrolysate composition of claim 1, having a dry matter content of at least 45%.

5. The concentrated hydrolysate composition of claim 1, having a dry matter content of at least 52%.

6. The concentrated hydrolysate composition of claim 1, having a dry matter content of at least 55%.

7. The concentrated hydrolysate composition of claim 1, having a dry matter content of at least 59%.

8. The concentrated krill protein hydrolysate fraction of claim 1, having less than 5% krill lipids on dry matter basis.

9. The concentrated krill protein hydrolysate fraction of claim 1, having aqueous soluble krill proteins.

* * * * *

UNITED STATES PATENT AND TRADEMARK OFFICE
CERTIFICATE OF CORRECTION

| | |
|---|---|
| PATENT NO. | : 9,167,832 B2 |
| APPLICATION NO. | : 14/074392 |
| DATED | : October 27, 2015 |
| INVENTOR(S) | : Stig Tore Kragh Jansson et al. |

It is certified that error appears in the above-identified patent and that said Letters Patent is hereby corrected as shown below:

On The Title Page, Item (73) should read

--Assignee:
Emerald Fisheries AS
Alesund, Norway--

Signed and Sealed this
Eighth Day of March, 2016

Michelle K. Lee
*Director of the United States Patent and Trademark Office*